United States Patent
Baurichter et al.

(10) Patent No.: US 9,576,692 B2
(45) Date of Patent: Feb. 21, 2017

(54) METHOD AND DEVICE FOR PRODUCING $^{99m}$Tc

(75) Inventors: Arnd Baurichter, Odense (DK); Oliver Heid, Erlangen (DE); Timothy Hughes, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 587 days.

(21) Appl. No.: 13/576,475

(22) PCT Filed: Jan. 20, 2011

(86) PCT No.: PCT/EP2011/050728
§ 371 (c)(1),
(2), (4) Date: Aug. 1, 2012

(87) PCT Pub. No.: WO2011/092102
PCT Pub. Date: Aug. 4, 2011

(65) Prior Publication Data
US 2012/0314828 A1 Dec. 13, 2012

(30) Foreign Application Priority Data
Feb. 1, 2010 (DE) .................. 10 2010 006 435

(51) Int. Cl.
*G21G 1/10* (2006.01)
*A61K 51/02* (2006.01)
(Continued)

(52) U.S. Cl.
CPC ............. *G21G 1/10* (2013.01); *A61K 51/025* (2013.01); *C01G 99/003* (2013.01); *G21G 1/001* (2013.01); *G21G 2001/0042* (2013.01)

(58) Field of Classification Search
CPC . G21G 1/10; G21G 2001/0042; A61K 51/025
(Continued)

(56) References Cited

U.S. PATENT DOCUMENTS 3,382,152 A * 5/1968 Lieberman et al. .......... 376/186
3,920,545 A * 11/1975 Argabright et al. .......... 210/670
(Continued)

FOREIGN PATENT DOCUMENTS

CN 1166228 A 11/1997 ............... G21G 1/10
EP 0776595 B1 12/1998 ............... G01G 1/10
(Continued)

OTHER PUBLICATIONS

Scholten et al, "Excitation functions for the cyclotron production of 99mTc and 99Mo", Applied Radiation and Isotopes, 51 (1999) 69-80.*
(Continued)

*Primary Examiner* — Jack W Keith
*Assistant Examiner* — Daniel Wasil
(74) *Attorney, Agent, or Firm* — Slayden Grubert Beard PLLC

(57) ABSTRACT

A method for producing $^{99m}$Tc may include: providing a solution comprising $^{100}$Mo-molybdate-ions; providing a proton beam having an energy suitable for inducing a $^{100}$Mo(p,2n)$^{99m}$Tc-nuclear reaction when exposing $^{100}$Mo-molybdate-ions; exposing the solution to the proton beams and inducing a $^{100}$Mo(p,2n)$^{99m}$Tc-nuclear reaction; and applying an extraction method for extracting the $^{99m}$Tc from the solution. Further, a device for producing $^{99m}$Tc may include: a solution with $^{100}$Mo-molybdate-ions; an accelerator for providing a proton beam with energy which is suitable for inducing a $^{100}$Mo(p,2n)$^{99m}$Tc-nuclear reaction when exposing $^{100}$Mo-molybdate-ions, for exposing the solution and for inducing a $^{100}$Mo(p,2n)$^{99m}$Tc-nuclear reaction; and an extraction step for extracting $^{99m}$Tc from the solution.

11 Claims, 3 Drawing Sheets

(51) Int. Cl.
*C01G 99/00* (2010.01)
*G21G 1/00* (2006.01)

(58) Field of Classification Search
USPC .......................................... 376/186, 194, 195
See application file for complete search history.

(56) References Cited

U.S. PATENT DOCUMENTS

| | | | | |
|---|---|---|---|---|
| 3,957,946 | A * | 5/1976 | Ronzio et al. | 423/56 |
| 4,046,852 | A * | 9/1977 | Vertes et al. | 423/58 |
| 4,107,044 | A * | 8/1978 | Levendusky | 210/682 |
| 4,158,700 | A * | 6/1979 | Karageozian | 423/2 |
| 4,276,267 | A * | 6/1981 | Bentley et al. | 376/195 |
| 5,049,256 | A * | 9/1991 | Luce | 210/772 |
| 5,116,470 | A | 5/1992 | Mausner et al. | 204/157.21 |
| 5,784,423 | A * | 7/1998 | Lidsky et al. | 376/156 |
| 5,802,439 | A * | 9/1998 | Bennett et al. | 376/189 |
| 5,874,811 | A * | 2/1999 | Finlan et al. | 376/195 |
| 5,910,971 | A * | 6/1999 | Ponomarev-Stepnoy et al. | 376/186 |
| 8,557,119 | B1 * | 10/2013 | Howe et al. | 210/681 |
| 2003/0016775 | A1 * | 1/2003 | Jamriska et al. | 376/195 |
| 2003/0058980 | A1 * | 3/2003 | El-Sharaway | 376/195 |
| 2005/0072735 | A1 * | 4/2005 | Stoller et al. | 210/651 |
| 2005/0082469 | A1 * | 4/2005 | Carlo | 250/262 |
| 2006/0011825 | A1 | 1/2006 | Pirozhenko et al. | 250/251 |
| 2006/0079410 | A1 * | 4/2006 | Yadav | 508/165 |
| 2006/0104401 | A1 * | 5/2006 | Jongen et al. | 376/190 |
| 2007/0062878 | A1 * | 3/2007 | Klipper et al. | 210/661 |
| 2007/0160176 | A1 * | 7/2007 | Wada | 376/158 |
| 2008/0187489 | A1 * | 8/2008 | Tomlison et al. | 422/159 |
| 2009/0060812 | A1 * | 3/2009 | Schenter et al. | 423/249 |
| 2010/0215137 | A1 * | 8/2010 | Nagai et al. | 376/158 |
| 2010/0266083 | A1 * | 10/2010 | Bloomquist et al. | 376/202 |
| 2011/0002431 | A1 * | 1/2011 | Johnson et al. | 376/194 |
| 2011/0280357 | A1 * | 11/2011 | Stevenson | 376/195 |
| 2012/0314828 | A1 | 12/2012 | Baurichter et al. | 376/195 |

FOREIGN PATENT DOCUMENTS

| | | | | |
|---|---|---|---|---|
| EP | 2104113 | * | 9/2009 | |
| EP | 2104113 | A1 | 9/2009 | G01G 1/02 |
| EP | 2242062 | A2 | 10/2010 | G01G 1/02 |
| GB | 2016796 | A | 9/1979 | G01G 4/04 |
| JP | 54133295 | A | 10/1979 | G01G 99/00 |
| JP | 10504681 | A | 5/1998 | G01G 1/10 |
| JP | 2008102078 | A | 5/2008 | G01G 4/08 |
| RU | 2118858 | C1 | 9/1998 | B01D 11/04 |
| WO | 2009/142669 | A2 | 11/2009 | G21G 1/10 |
| WO | 2011/092102 | A1 | 8/2011 | A61K 51/02 |

OTHER PUBLICATIONS

Lagunas-Solar, "Accelerator production of 99mTc with proton beams and enriched 100Mo targets", IAEA, Feb. 1999.*

Lagunas-Solar, Manuel et al., "Cyclotron Production of NCA $^{99m}$Tc and $^{99}$Mo. An Alternative Non-reactor Supply Source of Instant $^{99m}$Tc and $^{99}$Mo→$^{99m}$Tc Generators," Appl. Radiat. Isot., vol. 42, No. 7, 15 pages, Nov. 8, 1990.

Takács, S. et al., "Evaluation of Proton Induced Reactions on $^{100}$Mo: New Cross Sections for Production of $^{99M}$Tc and $^{99}$Mo," Journal of Radioanalytical and Nuclear Chemistry, vol. 257, No. 1, Springer, 7 pages, Nov. 6, 2002.

Guérin, B. et al., "Comparing Cyclotron-Produced Tc-99m with Generator-Produced Tc-99m," Abstracts: Nuclear Medicine and Biology, vol. 37, No. 6, Elsevier, 2 pages, Aug. 1, 2010.

International Search Report and Written Opinion, Application No. PCT/EP2011/050728, 19 pages, Apr. 6, 2011.

Russian Office Action, Application No. 2012137210, 11 pages, Dec. 5, 2014.

* cited by examiner

METHOD AND DEVICE FOR PRODUCING $^{99m}$Tc

CROSS-REFERENCE TO RELATED APPLICATIONS

This application is a U.S. National Stage Application of International Application No. PCT/EP2011/050728 filed Jan. 20, 2011, which designates the United States of America, and claims priority to DE Patent Application No. 10 2010 006 435.1 filed Feb. 1, 2010. The contents of which are hereby incorporated by reference in their entirety.

TECHNICAL FIELD

This disclosure relates to a method and a device for producing $^{99m}$Tc. $^{99m}$Tc is used, inter alia, in medical imaging, for example in SPECT imaging.

BACKGROUND

A commercially available $^{99m}$Tc generator is an instrument for extracting the metastable isotope $^{99m}$Tc from a source which contains decaying $^{99}$Mo.

$^{99}$Mo in turn is usually obtained from a method which uses highly enriched uranium $^{235}$U as a target. $^{99}$Mo is created as a fission product by irradiating the target with neutrons. However, as a result of international treaties, it will become ever more difficult in future to operate reactors with highly enriched uranium, which could lead to shortages in the supply of radionuclides for SPECT imaging.

SUMMARY

In one embodiment, a method for producing $^{99m}$Tc may comprise: providing a solution with $^{100}$Mo-molybdate ions, providing a proton beam with an energy suitable for inducing a $^{100}$Mo(p,2n)$^{99m}$Tc nuclear reaction when $^{100}$Mo-molybdate ions are irradiated, irradiating the solution with the proton beam and inducing a $^{100}$Mo(p,2n)$^{99m}$Tc nuclear reaction, and applying an extraction method for extracting the $^{99m}$Tc from the solution. In a further embodiment, the extraction method is a solvent extraction method, more particularly using methyl ethyl ketone. In a further embodiment, the dissolved $^{100}$Mo-molybdate ions remaining after the $^{99m}$Tc extraction are returned to the solution to be irradiated. In a further embodiment, the solution with $^{100}$Mo-molybdate ions is a solution of a $^{100}$Mo-molybdate salt, wherein a nuclear reaction which leads to at least one cation end product is induced in the solution by irradiation with the proton beam at the cations of the $^{100}$Mo-molybdate salt. In a further embodiment, after extracting the $^{99m}$Tc, the remaining, dissolved $^{100}$Mo-molybdate ions are returned to the irradiating solution and the at least one cation end product is removed before the supply, more particularly by using an ion exchanger. In a further embodiment, after extracting the $^{99m}$Tc from the solution, the extracted $^{99m}$Tc is cleansed of impurities resulting from the cation end product, more particularly by using an ion exchanger. In a further embodiment, the $^{100}$Mo-molybdate salt comprises $^{6}$Li$_2$$^{100}$MoO$_4$, and wherein the at least one cation end product comprises $^{3}$H. In a further embodiment, the Mo-molybdate salt comprises Na$_2$$^{100}$MoO$_4$, and wherein the cation end product comprises $^{18}$F. In a further embodiment, the $^{100}$Mo-molybdate salt comprises K$_2$$^{100}$MoO$_4$, and wherein the cation end product comprises Ca ions.

In another further embodiment, a device for producing $^{99m}$Tc may comprise: a solution with $^{100}$Mo-molybdate ions, an accelerator for providing a proton beam with an energy suitable for inducing a $^{100}$Mo(p,2n)$^{99m}$Tc nuclear reaction when $^{100}$Mo-molybdate ions are irradiated, for irradiating the solution and for inducing a $^{100}$Mo(p,2n)$^{99m}$Tc nuclear reaction, and an extraction stage for extracting the $^{99m}$Tc from the solution. In a further embodiment, the dissolved $^{100}$Mo-molybdate ions remaining after the $^{99m}$Tc extraction can be returned to the solution to be irradiated by a loop. In a further embodiment, the solution with $^{100}$Mo-molybdate ions is a solution of a $^{100}$Mo-molybdate salt, wherein a nuclear reaction which leads to at least one cation end product is induced in the solution by irradiation with the proton beam at the cations of the $^{100}$Mo-molybdate salt. In a further embodiment, the device additionally has a first cleaning stage downstream of the extraction stage, in which cleaning stage the extracted $^{99m}$Tc can be cleansed of impurities resulting from the cation end product. In a further embodiment, the device additionally has a second cleaning stage, in which the at least one cation end product is removed, more particularly by using an ion exchanger, before the remaining, dissolved $^{100}$Mo-molybdate ions are supplied to the solution to be irradiated.

BRIEF DESCRIPTION OF THE DRAWINGS

Example embodiments will be explained in more detail below with reference to figures, in which.

DETAILED DESCRIPTION

Figure 1:
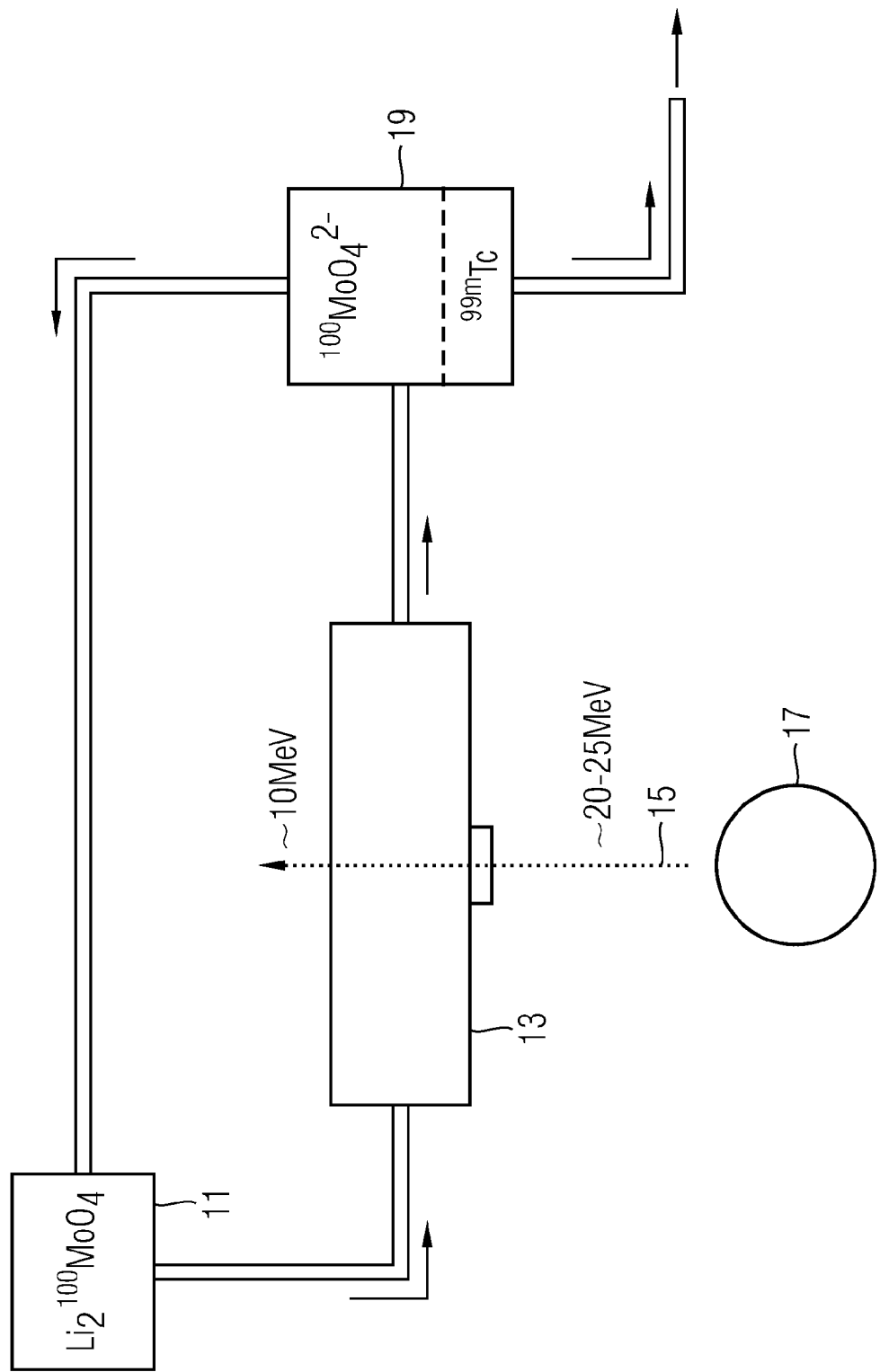
FIG. 1 shows the design of a device for producing $^{99m}$Tc from a lithium-molybdate salt, according to one embodiment.

Some embodiment provide a method and a device for the alternative production of $^{99m}$Tc.

For example, in some embodiments a method for producing $^{99m}$Tc comprises:
  providing a solution with $^{100}$Mo-molybdate ions,
  providing a proton beam with an energy suitable for inducing a $^{100}$Mo(p,2n)$^{99m}$Tc nuclear reaction when $^{100}$Mo-molybdate ions are irradiated,
  irradiating the solution with the proton beam and inducing a $^{100}$Mo(p,2n)$^{99m}$Tc nuclear reaction,
  applying an extraction method for extracting the $^{99m}$Tc from the solution.

Thus, the $^{99m}$Tc is obtained directly on the basis of a nuclear reaction which occurs as a result of the interaction of the proton beam with the molybdenum atoms, according to the equation $^{100}$Mo(p,2n)$^{99m}$Tc. The energy of the proton beam is greater than 20 MeV and is therefore in a range in which the effective cross section for the aforementioned nuclear reaction lies. As a result, $^{99m}$Tc atoms can be obtained in a number that is sufficient for the production of $^{99m}$Tc. As a result of the fact that the molybdenum atoms are present as molybdate ions in a solution, the resultant $^{99m}$Tc can subsequently be extracted from the solution in a simple manner with the aid of an extraction method. The extracted $^{99m}$Tc can then be used for different purposes, in particular for producing a radionuclide for SPECT imaging.

The proton beam is accelerated to an energy of at least 20 MeV. The particle beam may be accelerated to an energy of 20 MeV to 25 MeV. Restricting the maximum energy to no more than 35 MeV, more particularly to 30 MeV and most particularly to 25 MeV avoids nuclear reactions leading to undesired reaction products, e.g. Tc isotopes other than $^{99m}$Tc, being triggered as a result of a particle beam with too high an energy, which would then again require an additional step by means of which the undesired reaction products are removed again. The chamber in which the solution with molybdate ions is contained can be designed or dimensioned such that the emerging particle beam has an energy of at least 10 MeV. In this manner, the energy range of the proton beam can be kept in a range in which the occurring nuclear reactions remain controllable and in which undesired reaction products merely occur to an acceptable extent.

Accelerating protons to the aforementioned energy usually requires only a single accelerator unit of average size, which can also be installed and used locally. Using the above-described method, $^{99m}$Tc can be produced locally in the vicinity or in the surroundings of the desired location of use, for example in a hospital environment. In contrast to conventional, non-local production methods which are accompanied by the use of large installations such as in nuclear reactors and the distribution problems connected therewith, local production solves many problems. Nuclear medicine units can plan their workflows independently from one another and are not reliant on complex logistics and infrastructure.

In one embodiment, the extraction method can be a liquid-liquid extraction method, more particularly using methyl ethyl ketone.

This extraction method is suitable because $^{99m}$Tc is present in a solution. The $^{99m}$Tc dissolves in methyl ethyl ketone, with the molybdate ions continuing to remain in the aqueous solution. This makes it possible to separate the $^{99m}$Tc from the $^{100}$Mo. The $^{99m}$Tc-loaded methyl ethyl ketone can e.g. be dried such that the $^{99m}$Tc can subsequently be used e.g. for producing a radiopharmaceutical.

In one embodiment, the dissolved $^{100}$Mo-molybdate ions remaining after the $^{99m}$Tc extraction can be returned to the solution to be irradiated, for example in a closed loop. This may ensure that the parent material, namely the $^{100}$Mo-molybdate ions, is used particularly efficiently.

In one embodiment, the solution with $^{100}$Mo-molybdate ions is a solution of a $^{100}$Mo-molybdate salt, wherein a nuclear reaction which leads to at least one cation end product is induced in the solution by irradiation with the proton beam at the cations of the $^{100}$Mo-molybdate salt, said reaction more particularly leading to a cation end product, which was not present in the original solution to be irradiated, which is an ion which is unstable and/or which is potentially harmful to the human body. The term "cation end product" does not necessarily mean that the end product has to be a cation, it merely denotes the fact that the end product originates from the cations of the salt.

In this case, the remaining, dissolved $^{100}$Mo-molybdate ions can be returned to the irradiating solution after extracting the $^{99m}$Tc, wherein the at least one cation end product is removed before the supply, more particularly by using an ion exchanger.

This embodiment can be advantageous in that the solution returned to the solution to be irradiated contains no constituents which, in the case of renewed irradiation by the proton beam, would lead to further irradiation products that differ from the cation end products. By way of example, it is then possible to avoid cation end products being supplied to the solution which, in the case of irradiation, would lead to further, new nuclear reactions. This makes it possible to avoid uncontrolled or unmanageable nuclear reactions despite the return of the molybdate ions.

In one embodiment, the extracted $^{99m}$Tc can be cleansed of impurities resulting from the cation end product, more particularly by using an ion exchanger.

This makes it possible, for example, to remove potentially undesired constituents of the extracted $^{99m}$Tc solution before further processing. Thus, for example, it is possible to remove potential substances which are toxic to the human body prior to the production of the radionuclide or other radionuclides with a different half-life.

In one embodiment variant, the $^{100}$Mo-molybdate salt comprises $^{6}$Li$_2$$^{100}$MoO$_4$. $^{6}$Li decays by the nuclear reaction $^{6}$Li(p,3He)$^{4}$H to $^{4}$H, which in turn immediately decays to tritium.

If $^{7}$Li were used, the bombardment by the proton beam would trigger the reaction $^{7}$Li(p,n)$^{7}$Be, with the $^{7}$Be having to be removed again. The use of $^{6}$Li avoids this.

As a result of this, no cation end product is created which, in the case of renewed irradiation by the proton beam, would lead to an uncontrolled chain of nuclear reactions. The cleaning stage, by means of which the cation end product being created is removed, can optionally be dispensed with.

In another embodiment variant, the $^{100}$Mo-molybdate salt comprises Na$_2$$^{100}$MoO$_4$. Here, the at least one cation end product comprises $^{18}$F. Naturally occurring $^{23}$Na is converted into $^{23}$Mg by bombardment with the proton beam as a result of the reaction $^{23}$Na(p,n)$^{23}$Mg, with said $^{23}$Mg in turn quickly decaying to $^{23}$Na. A further nuclear reaction is $^{23}$Na(p,x)$^{18}$F. Overall, $^{18}$F is now also present as a cation end product after the irradiation, said $^{18}$F not having been present in the original solution. The $^{18}$F can be removed with the aid of an ion exchanger, for example from the solution which contains the $^{99m}$Tc after the extraction of $^{99m}$Tc or from the solution which contains the remaining molybdate after the extraction of $^{99m}$Tc and which is returned to the original solution. As a result, this avoids the irradiation of $^{18}$F and the return loop triggering a chain of nuclear reactions which are difficult to control.

In a further embodiment variant, the $^{100}$Mo-molybdate salt comprises K$_2$$^{100}$MoO$_4$, with the cation end product comprising $^{41}$Ca. Naturally occurring $^{41}$K is converted by the proton beam in the following nuclear reactions: $^{41}$K(p,n)$^{41}$Ca, $^{41}$K(p,γ)$^{42}$Ca, $^{41}$K(p,αγ)$^{38}$Ar. $^{39}$K, which likewise occurs naturally, is converted by the proton beam in the following nuclear reactions: $^{39}$K(p,d)$^{38}$K, $^{39}$K(p,γ)$^{40}$Ca. $^{38}$K decays to $^{38}$Ar. Of all the Ca ions created, only $^{41}$Ca is unstable. All ions can be removed by the ion exchanger. Returning $^{38}$Ar is uncritical because the interaction cross section for the interaction with the proton beam is in a different region than the interaction cross section for the $^{100}$Mo(p,2n)$^{99m}$Tc nuclear reaction. Returning and irradiating $^{38}$Ar therefore does not create a nuclear reaction chain with uncontrollable end products.

In some embodiments, a device for producing $^{99m}$Tc comprises:
  a solution with $^{100}$Mo-molybdate ions,
  an accelerator for providing a proton beam with an energy suitable for inducing a $^{100}$Mo(p,2n)$^{99m}$Tc nuclear reaction when $^{100}$Mo-molybdate ions are irradiated, for irradiating the solution and for inducing a $^{100}$Mo(p,2n)$^{99m}$Tc nuclear reaction,
  an extraction stage for extracting the $^{99m}$Tc from the solution.

In one embodiment variant, the solution with $^{100}$Mo-molybdate ions is a solution of a $^{100}$Mo-molybdate salt, wherein a nuclear reaction which leads to at least one cation end product is induced in the solution by irradiation with the proton beam at the cations of the $^{100}$Mo-molybdate salt and wherein the device additionally has a first cleaning stage downstream of the extraction stage, in which cleaning stage the extracted $^{99m}$Tc can be cleansed of impurities resulting from the cation end product.

In one embodiment variant, provision is made for a loop, by means of which the dissolved $^{100}$Mo-molybdate ions of the solution to be irradiated, which remain after the extraction of $^{99m}$Tc, can be resupplied, for example via a closed loop. More particularly, if the solution with $^{100}$Mo-molybdate ions is a solution of a $^{100}$Mo-molybdate salt, the device can additionally have a cleaning stage, interposed into the loop, in which the at least one cation end product is removed, more particularly by using an ion exchanger, before the remaining, dissolved $^{100}$Mo-molybdate ions are supplied.

According to the embodiment of FIG. 1, an aqueous solution 11 is initially provided, in which $^6\text{Li}_2{}^{100}\text{MoO}_4$ is dissolved.

The solution 11 is subsequently routed to an irradiation chamber 13, which is irradiated by a proton beam 15 which is generated by an accelerator unit 17 such as e.g. a cyclotron. Here, the proton beam 15 has an energy of 20 to 25 MeV on entry into the irradiation chamber 13, and an energy of approximately 10 MeV upon exit. In this energy range, the proton beam 15 interacts with the $^{100}$Mo and partly converts the latter directly into $^{99m}$Tc in a nuclear reaction, on the basis of the nuclear reaction $^{100}$Mo(p,2n)$^{99m}$Tc.

As a result of irradiating the $^6$Li ions, the following nuclear reactions also occur: $^6$Li(p,3He)$^4$H, with $^4$H immediately decaying to tritium.

The irradiated solution is routed to a chamber 19 for solvent extraction, in which the $^{99m}$Tc is extracted from the aqueous solution with the aid of MEK (methyl ethyl ketone). The $^{99m}$Tc dissolved in MEK can then be processed further, for example in a subsequent pharmaceutical module (not illustrated).

The remaining solution of the molybdate salt is returned to the originally provided solution 11.

Figure 2:
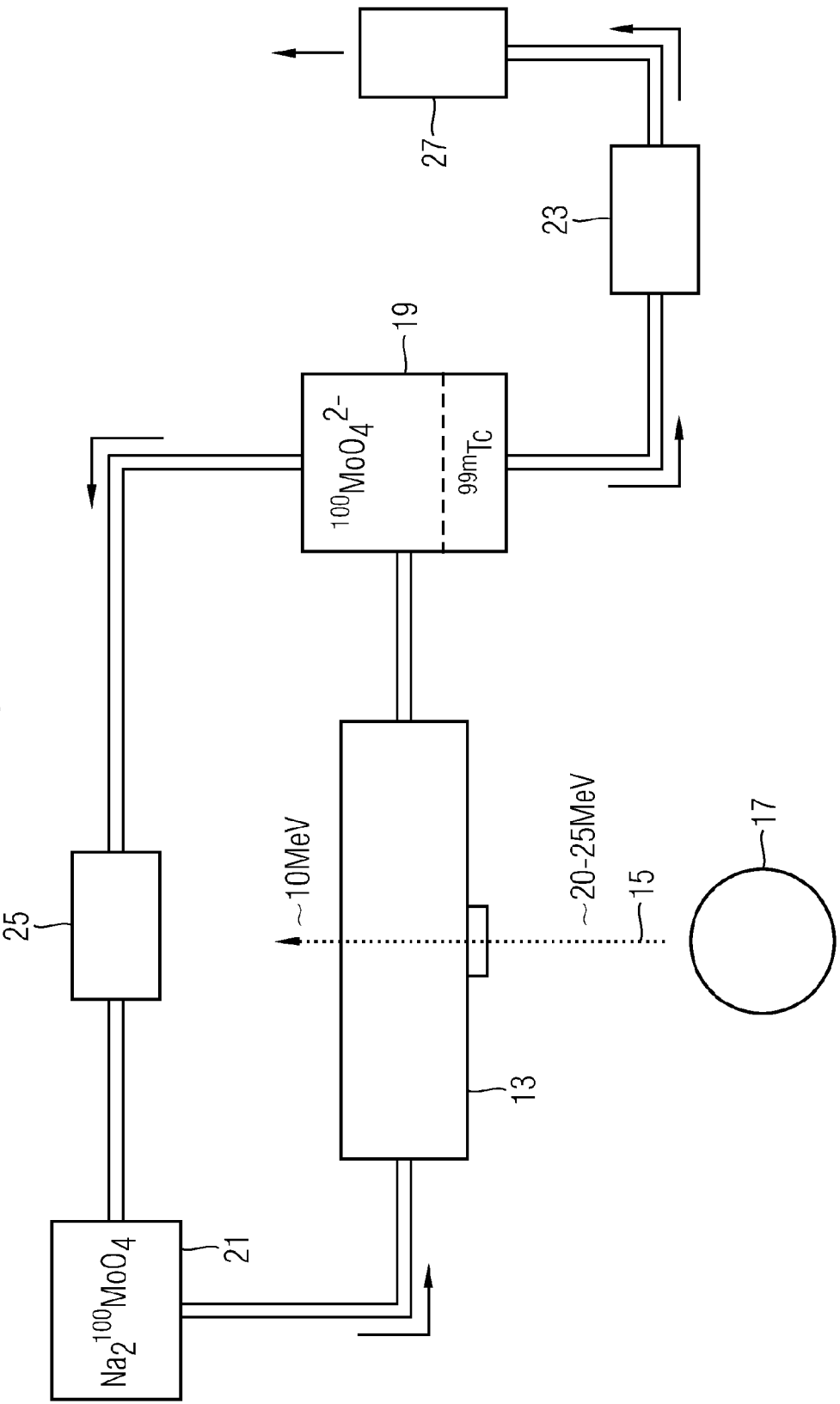
FIG. 2 shows the design of a device for producing $^{99m}$Tc from a sodium-molybdate salt, according to one embodiment.

The embodiment in FIG. 2 differs from FIG. 1 by virtue of the fact that an aqueous solution 21 is initially provided, in which $\text{Na}_2{}^{100}\text{MoO}_4$ is dissolved.

As a result of irradiating the Na ions, the following nuclear reactions occur: $^{23}$Na(p,n)$^{23}$Mg and $^{23}$Na(p,x)$^{18}$F. $^{23}$Mg in turn decays to stable $^{23}$Na. By contrast, $^{18}$F is radioactive.

The irradiated solution is routed to a chamber 19 for solvent extraction, in which the $^{99m}$Tc is extracted from the aqueous solution with the aid of MEK (methyl ethyl ketone). Prior to further processing, impurities resulting from the $^{18}$F can be removed with the aid of a first ion exchanger 23.

$^{18}$F can likewise be removed with the aid of a further ion exchanger 25, before the solution of the molybdate salt remaining after the $^{99m}$Tc extraction is returned to the originally provided solution 21.

The extracted $^{99m}$Tc solution 27, which has been cleansed of $^{18}$F, can then for example be made available in a subsequent pharmaceutical module.

Figure 3:
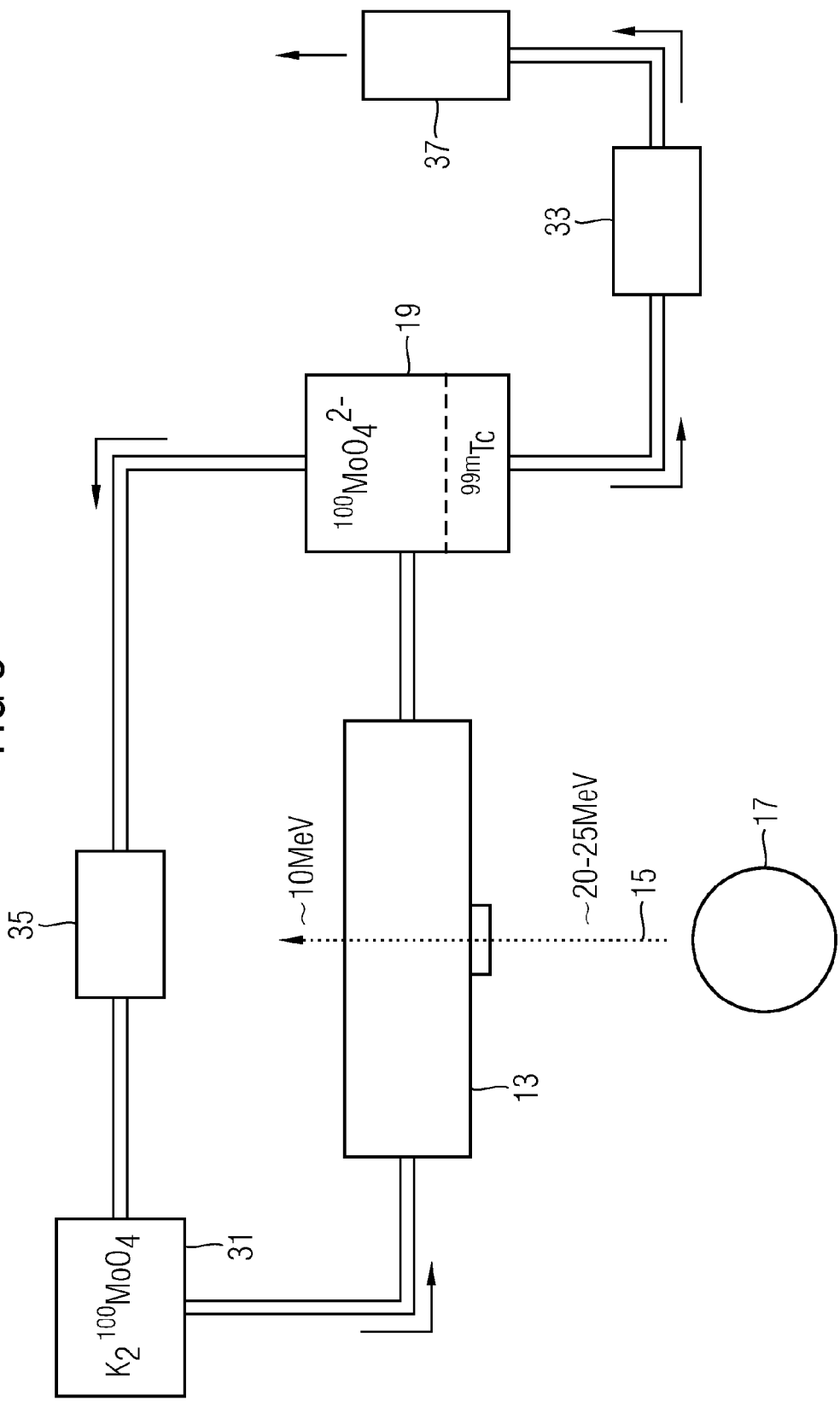
FIG. 3 shows the design of a device for producing $^{99m}$Tc from a potassium-molybdate salt, according to one embodiment.

The embodiment in FIG. 3 differs from FIG. 1 by virtue of the fact that an aqueous solution 31 is initially provided, in which $\text{K}_2{}^{100}\text{MoO}_4$ is dissolved.

As a result of irradiating the K ions, the following nuclear reactions occur: $^{41}$K(p,n)$^{41}$Ca, $^{41}$K(p,γ)$^{42}$Ca, $^{41}$K(p,αγ)$^{38}$Ar, $^{39}$K(p,d)$^{38}$K, $^{39}$K(p,γ)$^{40}$Ca. Of all the cation end products which are being created, only $^{41}$Ca is unstable.

The irradiated solution is routed to a chamber 19 for solvent extraction, in which the $^{99m}$Tc is extracted from the aqueous solution with the aid of MEK (methyl ethyl ketone).

Prior to further processing, impurities resulting from the $^{41}$Ca can be removed with the aid of a first ion exchanger 33.

The $^{41}$Ca and the other Ca ions can likewise be removed with the aid of a further ion exchanger 35 before the solution of the molybdate salt remaining after the $^{99m}$Tc extraction is returned to the originally provided solution 31.

The extracted $^{99m}$Tc solution, which has been cleansed of $^{41}$Ca, can then for example be dried in a dryer unit 37 and be made available in a subsequent pharmaceutical module (not illustrated).

LIST OF REFERENCE SIGNS 11, 21, 31 Aqueous solution
13 Irradiation chamber
15 Proton beam
17 Accelerator unit
19 Chamber for solvent extraction
23, 33 First ion exchanger
25, 35 Further ion exchangers
27 Cleansed $^{99m}$Tc solution 27
29 Dryer device

What is claimed is:

1. A method for producing $^{99m}$Tc, comprising:
    providing an aqueous solution comprising dissolved $^{100}$Mo-molybdate ions,
    providing a proton beam having an energy suitable for inducing a $^{100}$Mo(p,2n)$^{99}$Tc nuclear reaction when $^{100}$Mo-molybdate ions are irradiated,
    irradiating the aqueous solution with the proton beam and inducing a $^{100}$Mo(p,2n)$^{99}$Tc nuclear reaction,
    applying a solvent extraction method to dissolve the $^{99}$Tc into solution with the solvent and separate a resulting $^{99}$Tc-loaded solvent solution from the aqueous solution containing dissolved $^{100}$Mo-molybdate ions.

2. The method of claim 1, wherein the extraction method comprises a solvent extraction method using methyl ethyl ketone.

3. The method of claim 1, comprising recycling dissolved $^{100}$Mo-molybdate ions remaining in solution after the $^{99}$Tc extraction to additional aqueous solution to be irradiated.

4. The method of claim 1, wherein the aqueous solution with dissolved $^{100}$Mo-molybdate ions is an aqueous solution of a $^{100}$Mo-molybdate salt, and wherein a nuclear reaction which leads to at least one cation end product is induced in the aqueous solution by irradiating cations of the $^{100}$Mo-molybdate salt in solution with the proton beam.

5. The method of claim 4, comprising:
    after extracting the $^{99}$Tc, recycling the remaining solution containing dissolved $^{100}$Mo-molybdate ions to additional aqueous solution; and
    removing the at least one cation end product before returning to the aqueous solution.

6. The method of claim 4, comprising after extracting the $^{99}$Tc from the aqueous solution, cleansing the extracted $^{99m}$Tc of impurities resulting from the nuclear reaction which leads to at least one cation end product.

7. The method of claim 4, wherein the $^{100}$Mo-molybdate salt comprises $^6\text{Li}_2{}^{100}\text{MoO}_4$, and wherein the at least one cation end product comprises $^3$H.

8. The method of claim 4, wherein the $^{100}$Mo-molybdate salt comprises $Na_2{}^{100}MoO_4$, and wherein the cation end product comprises $^{18}$F.

9. The method of claim 4, wherein the $^{100}$Mo-molybdate salt comprises $K_2{}^{100}MoO_4$, and wherein the cation end product comprises Ca ions.

10. The method of claim 4, comprising after extracting the $^{99m}$Tc, returning the remaining dissolved $^{100}$Mo-molybdate ions to the aqueous solution and removing the at least one cation end product using an ion exchanger.

11. The method of claim 4, comprising after extracting the $^{99}$Tc from the aqueous solution, using an ion exchanger to cleanse the extracted $^{99}$Tc of impurities resulting from the at least one cation end product.

* * * * *